US00PP11717P

United States Patent [19]

Noodelijk

[11] Patent Number: Plant 11,717

[45] Date of Patent: Dec. 26, 2000

[54] CHRYSANTHEMUM PLANT NAMED 'HERMES'

[75] Inventor: Robert Noodelijk, Woubrugge, Netherlands

[73] Assignee: Chrysanthemum Breeders Association N.V., Netherlands

[21] Appl. No.: 09/179,455

[22] Filed: Oct. 27, 1998

[51] Int. Cl.[7] ..... A01H 5/00

[52] U.S. Cl. ..... Plt./287; Plt./286

[58] Field of Search ..... Plt./286, 287

*Primary Examiner*—Howard J. Locker

*Attorney, Agent, or Firm*—Parkhurst & Wendel, L.L.P.

[57] ABSTRACT

A chrysanthemum plant named Hermes characterized by its small sized blooms with purple ray florets and prolific branching; natural season flower date 4–7 September; blooming for a period of 7 weeks.

2 Drawing Sheets

BACKGROUND OF THE INVENTION

The new plant of the present invention comprises a new and distant cultivar of chrysanthemum plant that is a cross of unknown *Dendrathema grandiflora* parents. The new and distinct cultivar was a seedling resulting from the open pollination amount groups of chrysanthemum cultivars maintained under the control of the inventor for breeding purposes. The new and distinct cultivar was discovered and selected as one flowering plant by Rob Noodelijk on a cultivated field in Rijsenhout, Holland in September, 1996. The plant has been asexually reproduced by cuttings in greenhouses at Rijsenhout, Holland. The new cultivar has been found to retain its distinctive characteristics through successive propagations.

SUMMARY OF THE INVENTION

The present plant is a new and distinct variety of chrysanthenum of a small sized bloom and purple color.

BRIEF DESCRIPTION OF THE DRAWINGS

The present invention of a new and distinct variety of chrysanthemum is shown in the accompanying drawings, the color being as nearly true as possible with color photographs of this type.

DESCRIPTION OF THE INVENTION

Figure 1:
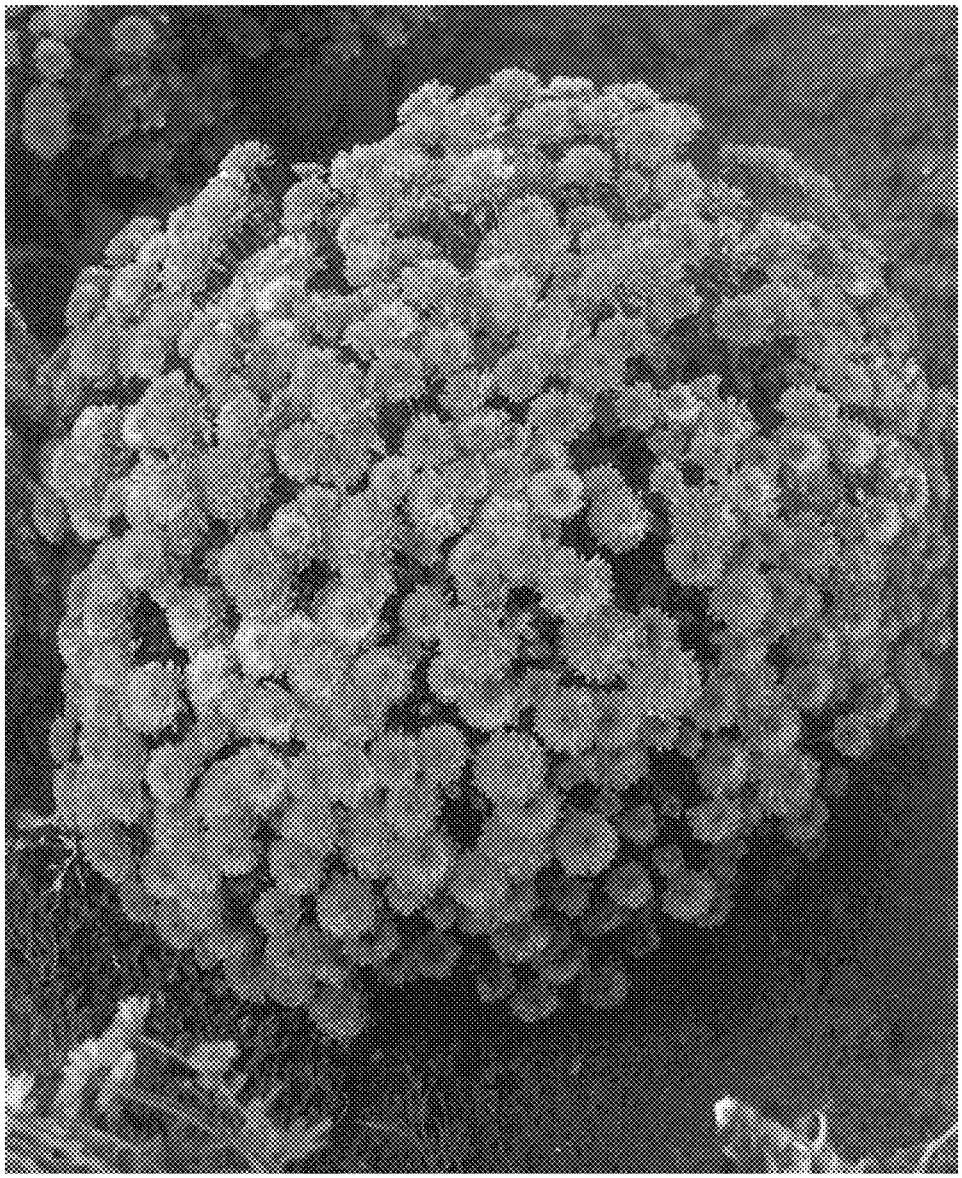
FIG. 1 shows a plant of the cultivar in full bloom.
Figure 2:
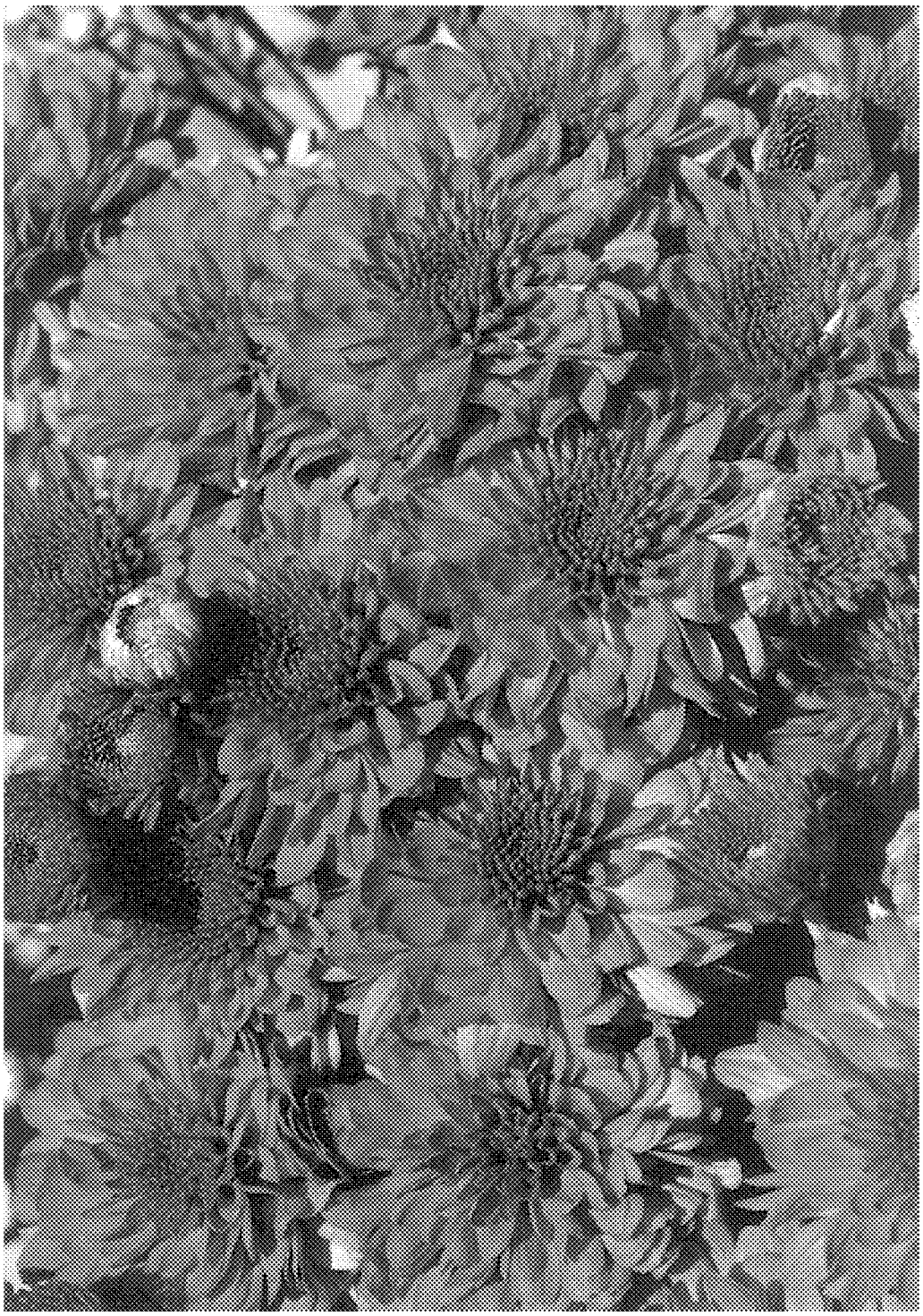
FIG. 2 shows the various stages of bloom of the new cultivar.

This new variety of chrysanthemum is of the botanical classification *Dendranthema grandiflora*. The observations and measurements were gathered from plants grown outdoors in Rijsenhout, Holland under natural day length and temperature and planted week 22 in 1997 and 1998. The natural blooming date of this crop was September 4–7 (week 36) with a photoperiodic response time of 49–51 days. The average height of the plants was 32–36 cms. This new variety produces small sized blooms with purple ray florets and yellow disc florets (only visible during bud and early stages of opening of the bloom).

The following is a description of the plant and characteristics that distinguish Hermes as a new and distinct variety.

The color designations (color designations are from The R.H.S. Colour Chart) are taken from the plant itself. Accordingly, any discrepancies between the color designations and the colors depicted in the photographs are due to photographic tolerances.

Botanical Classification

| CULTIVAR | HERMES |
|---|---|
| Bud | |
| Size | SMALL CROSS SECTION ± 1.0 CM HEIGHT ± 0.7 CM |
| Outside Color | RED-PURPLE 61 A |
| Bloom | |
| Size | SMALL |
| Fully Expanded | 4–4½ CM |
| Borne (number of) blooms per branch) | UPPER AND LOWER PORTION PLURAL BLOOMS PER BRANCH (APPROX. 6–8 BLOOMS) |
| Length of lateral branch | FROM TOP TILL BOTTOM APPROX. 15 CM |
| Lateral branch, Attachment | MEDIUM |
| Branching | Prolific with 6–8 breaks after pinching |
| Form | DECORATIVE |
| Performance (on the plant) | 7 WEEKS |
| Color | |
| Center of Flower | RED-PURPLE 61 A at mature stage When visible during bud and early stage of opening of the bloom Yellow 9 A |
| Color of the upper surface of the majority of the ray-florets | RED-PURPLE 61 B |
| Color of the flower surface of the majority of the ray-florets | PURPLE 75 C |
| Tonality from Distance | A VIGOROUS GARDENMUM WITH PURPLE DECORATIVE BLOOMS AND A SMALL YELLOW CENTER DURING BUD AND EARLY STAGES OF |

-continued

Botanical Classification

| CULTIVAR | HERMES |
|---|---|
| | OPENING OF THE BLOOM |
| Discoloration | TO PURPLE 75B |
| Ray florets | |
| Texture | UPPERSIDE SMOOTH UNDERSIDE SMOOTH |
| Number | ±210–230 |
| Cross-section | CONCAVE |
| Longitudinal axis of the majority | REFLEXING |
| Shape of tip | POINTED |
| Fragrance | TYPICAL CHRYSANTHEMUM |
| Disc Diameter (natural season crop when visible) | Approx. 0.5 cm |
| Reproductive Organs | |
| Stamen | NONE |
| Pollen | NONE |
| Styles (present in both ray and disc florets) | GREEN, THIN |
| Style Length | ±4 MM |
| Stigmas | YELLOW - GREEN |
| Stigma Width | ±1 MM |
| Ovaries | ENCLOSED IN CALYX |
| Plant | |
| Form | A GARDENMUM (POT MUM) MEANT FOR OUTDOOR USE |
| Growth | VIGOROUS |
| Height (from soil level) | ±32–36 CM |

-continued

Botanical Classification

| CULTIVAR | HERMES |
|---|---|
| Stem Color | GREEN 137 A |
| Stem Strength | STRONG |
| Stem Brittleness | PRESENT |
| Stem Anthocyanin Coloration | PRESENT |
| Natural blooming date | 4–7 September |
| Foliage | |
| Color | UPPERSIDE GREEN 137 A UNDERSIDE GREEN 138 B |
| Size | SMALL: LENGTH ± 5 CM WIDTH ±4 CM |
| Quantity (number per lateral branch) | 12–15 |
| Shape | EGG-SHAPED |
| Texture | FLESHY |
| Ribs and Veins | RIBS AND VEINS NOT SO WELL DEVELOPED |
| Edge | LOBED |
| Shape of Base of Sinus Between Lateral Lobes | ACUTE |
| Margin of Sinus Between Lateral Lobes | DIVERGING |
| Shape of Base | ACUTE |
| Apex | CUSPIDATE |

I claim:

1. A new and distinct variety of chrysanthemum plant as described and illustrated.

* * * * *